(12) United States Patent
Dübner et al.

(10) Patent No.: US 7,119,233 B2
(45) Date of Patent: Oct. 10, 2006

(54) METHOD FOR PREPARING 3-(METHYLTHIO)PROPANAL

(75) Inventors: Frank Dübner, Friedberg (DE); Christoph Weckbecker, Gründau-Lieblos (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/198,609

(22) Filed: Aug. 5, 2005

(65) Prior Publication Data

US 2006/0030739 A1  Feb. 9, 2006

(30) Foreign Application Priority Data

Aug. 5, 2004 (DE) .................... 10 2004 038 053

(51) Int. Cl.
*C07C 319/00* (2006.01)
*C07C 253/00* (2006.01)

(52) U.S. Cl. ........................................ 568/63; 558/335

(58) Field of Classification Search .................... None
See application file for complete search history.

(56) References Cited

U.S. PATENT DOCUMENTS

| 4,048,232 A | 9/1977 | Koberstein et al. |
|---|---|---|
| 4,225,515 A | 9/1980 | Weber et al. |
| 4,225,516 A | 9/1980 | Biola et al. |
| 4,319,047 A | 3/1982 | Komorn et al. |
| 4,440,676 A | 4/1984 | Cadogan et al. |
| 5,352,837 A | 10/1994 | Hsu et al. |
| 5,705,675 A | 1/1998 | Blackburn et al. |
| 5,905,171 A * | 5/1999 | Hsu .............................. 568/41 |
| 6,057,481 A * | 5/2000 | Brockwell et al. ............ 568/41 |

FOREIGN PATENT DOCUMENTS

| DE | 2 320 544 | 9/1974 |
|---|---|---|
| FR | 2 314 917 | 1/1977 |
| FR | 2 480 925 | 1/1981 |
| WO | WO 97/00858 | 1/1997 |
| WO | WO 03/009938 A2 | 2/2003 |

* cited by examiner

*Primary Examiner*—Sikarl A. Witherspoon
(74) *Attorney, Agent, or Firm*—Smith, Gambrell & Russell, LLP

(57) ABSTRACT

A method for preparing 3-(methylthio)propanal and 2-hydroxy-4-(methylthio)butanenitrile by catalyzed addition of methylmercaptan to acrolein and hydrogen cyanide to 3-(methylthio)propanal.

34 Claims, 2 Drawing Sheets

METHOD FOR PREPARING 3-(METHYLTHIO)PROPANAL

The invention relates to a catalytic method for preparing 3-(methylthio)propanal and 2-hydroxy-4-(methylthio)butanenitrile. In particular, the invention describes a process for synthesizing MMP and MMP-cyanohydrin using novel addition catalysts.

PRIOR ART 3-(Methylthio)propanal (MMP) and 2-hydroxy-4-(methylthio)butanenitrile (MMP-cyanohydrin) are intermediates for synthesizing D,L-methionine and the methioninehydroxy analogue 2-hydroxy-4-methylthiobutyric acid (MHA). Methionine is an essential amino acid which inter alia is used as supplement in feedstuffs. MHA is a liquid methionine substitute of low biological availability.

MMP is prepared by catalytic addition of methylmercaptan (Mc) to acrolein (Ac). Generally, liquid acrolein is reacted with methylmercaptan in a reactor in which liquid MMP and the catalyst are already present in dissolved form (DT 2320544). Also known is the use of gaseous acrolein with methylmercaptan (FR 7520183, FR 7917827, WO 97/00858). The reaction between methylmercaptan and acrolein can be carried out batchwise or continuously (U.S. Pat. No. 4,225,515, U.S. Pat. No. 5,352,837). As conventional catalysts, use is made of organic bases, e.g. tertiary amines such as hexamethylenetetramine, trialkylamines, e.g. triethyl- or triethanolamine, benzylamines, pyridines, e.g. 2-fluoropyridine and 4-dimethylaminopyridine, picoline, pyrazine, imidazole and nicotinamide, but also copper(II) acetate, mercury methylmercaptide and organic peroxides.

The use of ion exchangers has also been mentioned (FR 7520183). Customarily, the actual addition catalyst is combined with an auxiliary catalyst, an organic acid, e.g. acetic adic, citric acid or formic acid, or a mineral acid, e.g. sulfuric acid or phosphoric acid, to firstly inhibit the polymerization of acrolein, that is to say the formation of unwanted by-products, and secondly to increase the general yield by conditioning of the added base. The catalyst is not recovered and is lost during the workup.

Typical catalyst concentrations are 0.001 to 0.005 mol % based on methylmercaptan. The required amount of acid, typically acetic acid, is betwen 0.5 and 50 mol %. To simplify the MMP preparation method, catalyst and acid can be mixed in a premix and added as solution. The concentration of catalyst premix in the liquid MMP reaction medium is customarily 0.2 to 0.75 by weight. After the reaction is completed, MMP is separated from the auxiliary and by-products by distillation. During the workup by distillation of the addition product thus prepared, the catalyst premix is lost and, depending on boiling point, must be disposed of via the distillation bottom phase or the off-gas. In principle, portions of the catalyst or of the added acid can pass overhead during the distillation and contaminate the desired pure MMP.

From MMP, by reaction with hydrogen cyanide (prussic acid), with the use of suitable catalysts, the MMP-cyanohydrin 2-hydroxy-4-(methylthio)butanenitrile may be prepared. Suitable catalysts are abovementioned bases which also catalyze the addition of methylmercaptan to acrolein, e.g. pyridine or triethylamine. Hydrolysis of MMP-cyanohydrin by e.g. mineral acids produces MHA. Methionine is formed by reaction of MMP-cyanohydrin with ammoniumhydrogencarbonate with formation of hydantoin, which can be saponified by a base, e.g. potassium carbonate or sodium hydroxide. The liberation of methionine occurs with carbon dioxide or sulphuric acid.

OBJECT OF THE INVENTION

It was an object of this invention to provide a catalytic method which makes possible not only the addition of methylmercaptan to acrolein, but also the further reaction of the reaction product to form MMP-cyanohydrin without consuming the catalyst or an additional acid.

DESCRIPTION OF THE INVENTION

The invention is a method for preparing 3-(methylthio)propanal in which a novel catalyst system makes possible the addition of methylmercaptan to acrolein. In addition, the invention is a method in which this novel catalyst system catalyzes the reaction between MMP and prussic acid for synthesis of MMP-cyanohydrin.

In particular, the invention is a method for continuous preparation of MMP and MMP-cyanohydrin using heterogeneous catalysts which are insoluble in the reaction medium and are therefore not consumed. The addition of auxiliary catalysts such as organic acids, e.g. acetic acid, is not necessary.

The novel catalysts have the general formula (I)

(formula I)

where $R_1$ and $R_2$ are hydrogen, alkyl having chain lengths from $C_1$ to $C_{12}$, aryl or heteroaryl. $R_1$ can be different from $R_2$. X is a number from 0 to 6. A is a natural or synthetic resin, e.g. polystyrene. In particular, the polymer-bound bases from the series of the homologous dialkylaminoalkylpolystyrenes and dialkylaminomacroreticular resins are selected, particularly from dimethylaminoethylpolystyrene, diethylaminoethyl-polystyrene, dimethylaminomethylpolystyrene, diethylaminomethylmacroreticular resins, and especially diethylaminomethylpolystyrene. The said bases are already used in part in other fields of solid-phase chemistry (WO 03/009936, U.S. Pat. No. 4,440,676) and some are commercially available. Furthermore, the synthesis of special derivatives is possible in a simple manner from described resins, e.g. Merrifield resin.

Since the catalysts are soluble neither in the reaction product nor in one of the participating reaction partners, use may be made of any desired amount of catalyst for the reaction which leads to sufficient conversion rates and selectivities. To facilitate the reaction procedure, i.e. metering of the reaction partners, transport of the starting materials to the active centres of the catalyst and removal of the heat of reaction, a reaction medium should be present in which the catalyst is readily swellable. A resin is readily swellable in a solvent when it can absorb the same as its own mass up to five times its own mass of solvent. The resin increases its volume here with absorption of the solvent. Preferably, MMP or MMP-cyanohydrin itself can serve as matrix for the reaction. However, use can also be made of all customary solvents in which the reaction partners, but not the catalyst, are at least partially soluble, e.g. hydrocarbons, halogenated hydrocarbons or ethers. Reactive solvents such as water, alcohols and ketones which, together with the starting materials or the products, can form unwanted by-products are less suitable and may be used only with restrictions. Based on the active centres, in batch experiments for synthesizing MMP, a molar ratio of catalyst to acrolein of 0.001 to 0.02, preferably 0.001 to 0.01, particularly preferably 0.001 to 0.005 is suitable. In continuous reactions in which the reaction partners and the reaction medium flow continuously pass the catalyst, the ratio of acrolein mass to catalyst mass per hour (LHSV value, m/m·h) is from 0.1 to 100, preferably from 1 to 50, particularly preferably from 5 to 50.

The ratio of the reaction medium to acrolein is chosen in batch experiments as from 0.1 to 2. In continuous methods, the ratio of mass flow rate of reaction medium to acrolein should be from 0.5 to 20. To achieve a good conversion of the reactants and for achieving low degradation, the amounts of the starting materials used are controlled such that a slight excess of methylmercapan in the reaction mixture is maintained. The excess should be from 0.01 to 1%, preferably 0.05 to 0.2%, on a molar basis. An excess of acrolein leads to increased formation of high-boiling residues and is therefore not desirable.

When the reaction is carried out, pressure is not a critical factor. It can vary within wide limits. However, since an excessive pressure, by compression of the catalyst bed, can reduce its activity, pressures above 10 bar should be avoided. Preferably, the reaction is to be carried out at atmospheric pressure.

The reaction temperature, depending on pressure and reaction medium, can be selected from −20 to 100° C. At atmospheric pressure and with MMP as matrix, temperatures from 0 to 60° C. are suitable, in particular temperatures from 30 to 50° C. Above these temperatures, the selectivity with respect to MMP formation falls, below 0° C., in contrast, the reaction velocity is too low to be able to bring economic advantages.

In the case of batchwise production of MMP, in the reactor an initial content of MMP and/or reaction medium is charged. The catalyst is suspended in this reaction medium. It is necessary to allow the catalyst to swell in the reaction medium before the start of the reaction, that is to say at the first use, in order to enable the optimum accessibility of the active centres. Then the starting materials methylmercaptan and acrolein are introduced at the same time. The heat of reaction is removed by suitable internals or modifications.

It is advantageous first to charge approximately 10% of the methylmercaptan and only then to continue with introducing acrolein and the remaining methylmercaptan. Methylmercaptan dissolves with reaction heat, forming a hemithioacetal in MMP. In this manner a continuous excess of methylmercaptan is ensured during the reaction. An excess of methylmercaptan leads to higher selectivities and thus to minimizing high-boiling by-products. In the event of a sufficient charge of MMP, it is possible to charge all of the methylmercaptan and not add acrolein until after.

After the reaction is completed, the product is filtered off from the catalyst and if appropriate can be further purified. If the reaction product MMP is not soluble in the reaction medium, this MMP can be separated from the reaction medium by phase separation. The catalyst and the reaction medium can be reused in subsequent reactions without further swelling. When MMP is used as reaction medium, it is advantageous to discharge only a portion of the MMP formed and to retain a corresponding operating content together with the catalyst for following charges.

If the crude MMP is to be reacted further to form MMP-cyanohydrin, this is successful simply by adding equimolar amounts of prussic acid to the reaction medium containing invented catalyst. In the batchwise production, for this the complete reaction of the acrolein with methylmercaptan must be completed. Purification of the crude MMP is not necessary.

In continuous production, the prussic acid can be added at a point in the catalyst bed at which the conversion to the MMP is complete. A downstream reaction loop having a separate catalyst bed is also possible. To avoid unnecessary by-products, the reaction should be run with an excess of prussic acid. The molar excess of prussic acid based on MMP should be from 0.01 to 10%, preferably from 0.05 to 1%. The reaction temperature should be from 0 to 100° C., preferably from 20 to 70° C. Either liquefied or gaseous prussic acid can be used.

DETAILED DESCRIPTION OF INVENTION

Figure 1:
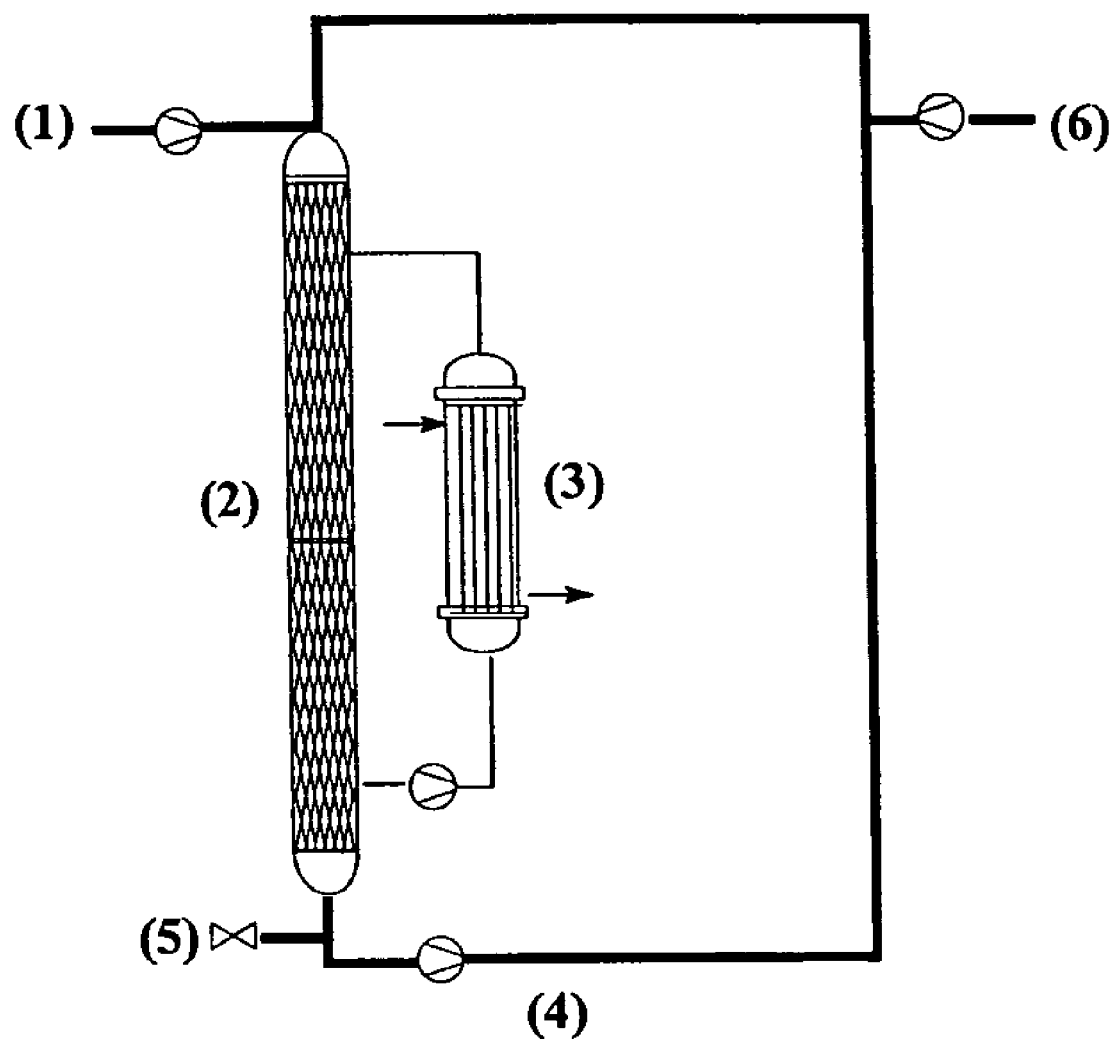
FIG. 1 shows a diagrammatic structure of a continuous production of MMP using the inventive heterogeneous solid-phase catalyst in a fixed-bed reactor.

In FIG. 1 the central apparatus is a fixed-bed reactor having catalyst packing (2) and circulation pump (4). On the circuit which also comprises a heat exchanger (3), metering devices for introducing methylmercaptan and acrolein (1) and an ejection (5) for taking off the resultant MMP reaction mixture are present. If the reaction medium is different from MMP, owing to the continuous ejection, a corresponding amount of the solvent taken off must be replenished into the reaction loop. Preferably, the methylmercaptan metering takes place upstream (6) of the acrolein addition. This ensures an excess in time of methylmercaptan at the start of the reaction. Nevertheless, it can be advantageous, in contrast to the necessary stoichiometry, to add on average a slight excess of methylmercaptan. The excess can be from 0.01 to 1%. Higher amounts do not lead to further improvement in acrolein yield.

The residence time of the reactants at the catalyst is determined via the catalyst volume and flow rate. Preferably, the ratio of acrolein mass to catalyst mass per hour (LHSV value, m/m·h) is from 0.1 to 100, preferably from 1 to 50, particularly preferably from 5 to 50. The mass ratio of reaction medium to acrolein should be from 1 to 20. The heat removal at the catalyst is controlled in such a manner that a temperature from 30 to 50° C. is achieved. The reaction is operated at atmospheric pressure. Elevated pressures are possible, but do not have an effect on conversion rate.

Figure 2:
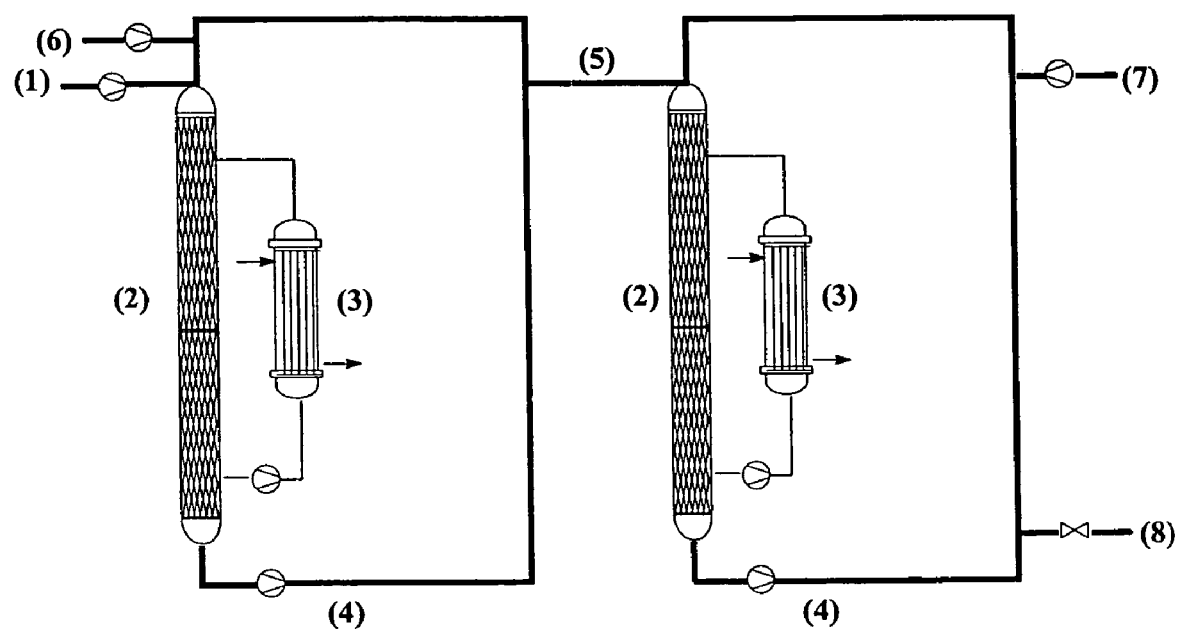
FIG. 2 shows a diagrammatic structure of continuous production of MMP using the inventive heterogeneous solid-phase catalyst in a fixed-bed reactor, extended for the reaction of MMP to form MMP-cyanohydrin with prussic acid metering and if appropriate a separate cyanohydrin reaction loop.

If the MMP produced is to be further reacted to form MMP-cyanohydrin, the structure is extended by prussic acid metering (7) or if appropriate by a separate cyanohydrin reaction loop as shown in FIG. 2.

The inventive method has the advantage of not consuming catalyst or catalyst aid. This is cost-efficient and sustained. In addition, the reaction product MMP (5) or MMP-cyanohydrin (8) is not contaminated by catalysts or catalyst aids. This firstly facilitates the workup of the products and secondly minimizes unwanted side reactions in following stages which are caused by remainders of the catalysts.

The present invention will be described in more detail hereinafter with reference to embodiment examples. These serve only to illustrate the invention and are in no way to be considered limiting in type and scope of these.

EXAMPLE 1

Synthesis of dimethylaminomethylpolystyrene resin 5 g (4.5 mmol) of Merrifield resin [CAS 55844-94-5] (0.9 mmol Cl/g), 6.9 g (50 mmol) of triethylamine and 200 ml of dimethylamine solution (400 mmol, 2 M in tetrahydrofuran, THF) are charged into a commercially conventional laboratory autoclave. The mixture is heated at 85° C. for a period of 5 hours. After cooling and depressurising the mixture is filtered off by suction through a glass frit and the filter cake is washed first chloride-free with water, and then rewashed with 200 ml of THF. The resin dried at 60° C. can, after swelling, be used directly in the following experiments. This produces 4.8 g of product which consists according to NMR of >90% of the dimethylbenzylamine-functionalized resin. In addition to unreacted benzyl chloride, benzyl alcohol is a minor functionality.

Batchwise synthesis of 3-(methylthio)propanal

In a reaction flask having dropping funnel and gas introduction, 0.5 g of dimethylaminomethylpolystyrene resin (activity approximately 18 mmol/1 MMP) are dispersed in 25 ml of distilled pure MMP as charge. The resin is allowed to swell for 1 h. At 0° C., in the course of 10 min, 10 g (208 mmol) of methylmercaptan are then passed in, which immediately dissolves with formation of an MMP-hemimercaptal. After introduction is completed, 11.5 g (205 mmol) of acrolein are added dropwise and further stirred at 0° C. After two hours, the catalyst is filtered off and the MMP analyzed. This produces an acrolein conversion rate of 98% and a yield of 95%. The residue in the bottom phase on distillation of the crude MMP is 0.19%.

The catalyst filtered off can be used directly in following experiments without further swelling. Use for ten times shows no loss of activity.

1.3 Batchwise synthesis of 2-hydroxy-4-(methylthio)-butanenitrile

For the further reaction with prussic acid, the catalyst is not filtered off, but prussic acid (12.6 g, 466 mmol, 1.05 equivalent) is added dropwise to the MMP reaction mixture with cooling at approximately 35° C. in the course of 30 min. After reaction is completed, the mixture is filtered off from the catalyst. This produces 62 g of MMP-cyanohydrin of a purity of >98%. The repeated reuse of the catalyst leads to no loss of activity.

1.4 Continuous synthesis of 3-(methylthio)propanal 4 mmol of dimethylaminomethylpolystyrene resin (equivalent to 4.4 g dry) previously swollen in MMP are packed into a reaction tube. The tubular reactor is connected into a circulation loop charged with pure MMP with a pump. The capacity in the loop is approximately 5 ml. A further pump permits the introduction of acrolein upstream of the reaction tube. In addition, a valve makes it possible to introduce liquid or gaseous methylmercaptan into the stream. An accompanying heat exchanger serves for heating the reaction loop to 50° C. To start the reaction 0.25 g of acrolein/min and 0.21 g of methylmercaptan/min are added. The volume fed to the reaction loop is removed at atmospheric pressure at a discharge point. The volumetric ratio of feed to circuit is ⅕. The reaction is in the steady state after approximately 30 min. Analysis of a representative crude MMP sample shows acrolein conversion rates >99% and MMP purities of approximately 93%.

The amount of MMP taken off from the reaction loop is reacted in a second reaction loop to give MMP-cyanohydrin. The set-up and procedure correspond to the above description for the reaction of acrolein with methylmercaptan. The amount of catalyst is 4 mmol, and the feed rate of HCN is 0.12 g/min. The volume fed to the reaction loop is taken off at atmospheric pressure at a discharge point. The volumetric ratio of feed to circuit is ⅕, and the temperature is maintained at 40° C. The reaction is in the steady state after approximately 30 min. Analysis of a representative MMP-cyanohydrin sample shows MMP conversion rates >99% and purities of approximately 92%.

EXAMPLE 2

2.1 Synthesis of diethylaminomethylpolystyrene resin

In a stirred flask having a reflux condenser, 30 g (27 mmol) of Merrifield resin [CAS 55844-94-5] (0.9 mmol Cl/g), 30.4 g (300 mmol) of triethylamine and 87.8 g (1.20 mol) of diethylamine are suspended in 420 ml of methyl isobutyl ketone. The mixture is kept at reflux for 6 hours. After it has cooled to room temperature it is filtered off by suction through a glass frit and the filtercake is washed chloride-free with water. The resin dried at 60° C. can, after swelling, be used directly in following experiments. This produces 32 g of product of which, according to NMR, >90% consists of the diethylbenzylamino-functionalized resin. In addition to unreacted benzyl chloride, benzyl alcohol is a minor functionality.

2.2 Batchwise synthesis of 3-(methylthio)propanal

Corresponding to the procedure of Example 1, 0.5 g of diethylaminomethylpolystyrene resin are reacted with acrolein and methylmercaptan.

After 2 hours this produces an acrolein conversion rate of >99% and a yield of >96%. The residue in the bottom phase in distillation of the crude MMP is 0.15%.

The further reaction to form MMP-cyanohydrin delivers this at conversion rates >99% at a purity of >95%.

The catalyst filtered off can be used directly without further swelling in the following experiments. Use for ten times shows no loss of activity.

2.3 Continuous synthesis of 3-(methylthio)propanal

Corresponding to the procedure from Example 1, 4.4 g (approximately 4 mmol) of diethylaminomethylpolystyrene resins are reacted with acrolein and methylmercaptan.

Analysis of a representative crude MMP sample shows acrolein conversion rates >99% and MMP purities of approximately 94%, while analysis of a representative MMP-cyanohydrin sample after addition of prussic acid shows MMP conversion rates >99% and purities of approximately 93%.

Further variations and modifications will be apparent to those skilled in the art from the foregoing and are intended to be encompassed by the claims appended hereto.

German priority document 10 2004 038053.8 is relied on and incorporated herein by reference.

EXPLANATIONS TO THE FIGURES (1) Input of acrolein
(2) Catalyst
(3) Heat exchanger
(4) Circulation pump
(5) Discharge of MMP
(6) Input of methylmercaptan
(7) Input of prussic acid
(8) Discharge of MMP-cyanohydrin

The invention claimed is:

1. A method for preparing 3-(methylthio)propanal comprising reacting methylmercaptan with acrolein in the presence of a) a heterogeneous catalyst, and b) a reaction medium, wherein the heterogeneous catalyst is not soluble in the reaction medium.

2. The method according to claim 1, wherein the heterogeneous catalyst has the formula

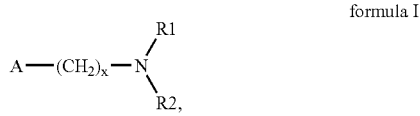

formula I where
R$_1$ and R$_2$ are hydrogen, alkyl having chain lengths from C$_1$ to C$_{12}$, aryl or heteroaryl;
R$_1$ can be different from R$_2$;
X is a number from 0 to 6; and
A is a natural or synthetic resin.

3. Method according to claim 2, wherein A in the formula I is a polystyrene.

4. The method according to claim 2, wherein the catalyst according to formula I is a polymer-bound base selected from the group consisting of the homologous dialkylaminoalkylpolystyrenes or dialkylaminomacroreticular resins.

5. The method according to claim 4, wherein the catalyst according to formula I is diethylaminoethylpolystyrene, diethylaminomethylpolystyrene, dimethylaminomethylpolystyrene, diethylaminomethylmacroreticular resin or dimethylaminoethylpolystyrene.

6. The method according to claim 1, wherein the reaction medium is a hydrocarbon, a halogenated hydrocarbon, an ether, 3-(methylthio)propanal or 2-hydroxy-4-(methylthio)butanenitrile.

7. The method according to claim 6, wherein the reaction medium is 3-(methylthio)propanal.

8. The method according to claim 1, wherein it is carried out at temperatures of −20° C. to 100° C.

9. The method according to claim 8, wherein the temperature is from 0° C. to 60° C.

10. The method according to claim 8, wherein the temperature is from 30° C. to 50° C.

11. The method according to claim 9, wherein the temperature is from 30° C. to 50° C.

12. The method according to claim 1, wherein, based on the active centers, the molar ratio of catalyst to acrolein is from 0.001 to 0.02.

13. The method according to claim 12, wherein the molar ratio of catalyst to acrolein is from 0.001 to 0.01.

14. The method according to claim 13, wherein the molar ratio of catalyst to acrolein is from 0.001 to 0.005.

15. The method according to claim 1, wherein the molar excess of methylmercaptan based on acrolein is from 0.01 to 1%.

16. The method according to claim 1, wherein the molar excess of methylmercaptan based on acrolein is from 0.05 to 0.2%.

17. The method according to claim 1, which is a batch method.

18. The method according to claim 17, wherein the ratio of reaction medium to acrolein is from 0.1 to 2.

19. The method according to claim 1, wherein the the method is continuous.

20. The method according to claim 19, wherein the ratio of flow rates by mass of reaction medium to acrolein is from 0.5 to 20.

21. A method for preparing 2-hydroxy-4-(methylthio)butanenitrile comprising reacting prussic acid with 3-(methylthio)propanal in the presence of a) a heterogeneous catalyst, and b) a reaction medium, wherein the heterogeneous catalyst is not soluble in the reaction medium.

22. The method according to claim 21, wherein the heterogeneous catalyst has the formula

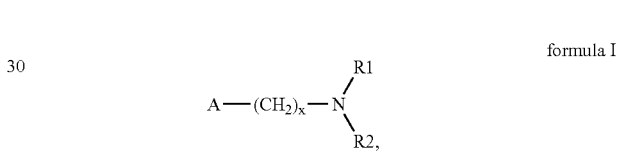

formula I where
R$_1$ and R$_2$ are hydrogen, alkyl having chain for C$_1$ to C$_{12}$, aryl or heteroaryl;
R$_1$ can be different from R$_2$
X is a number from 0 to 6, and
A is a natural or synthetic resin.

23. The method according to claim 20, wherein A in the formula I is a polystyrene.

24. The method according to claim 22, wherein the catalyst according to formula I is a polymer-bound base selected from the group consisting of the homologous dialkylaminoalkylpolystyrenes or dialkylaminomacroreticular resins.

25. The method according to claim 24, wherein the catalyst according to formula I is diethylaminoethylpolystyrene, diethylaminomethylpolystyrene, dimethylaminomethylpolystyrene, diethylaminomethylmacroreticular resin or dimethylaminoethylpolystyrene.

26. The method according to claim 21, wherein the reaction medium is a hydrocarbon, a halogenated hydrocarbon, an ether, or 2-hydroxy-4-(methylthio)butanenitrile.

27. The method according to claim 26, wherein the reaction medium is 2-hydroxy-4-(methylthio)butanenitrile.

28. The method according to claim 21, which is carried out at temperatures of 0° C. to 100° C.

29. The method according to claim 28, wherein the temperature is from 20° C. to 70° C.

30. The method according to claim 21, wherein the ratio of catalyst to 3-(methylthio)propanal is from 0.001 to 0.02.

31. The method according to claim 21, wherein the molar excess of prussic acid to 3-methylthio)propanal is from 0.01 to 10%.

32. The method according to claim 21, wherein the molar excess of prussic acid to 3-methylthio)propanal is from 0.05 to 1%.

33. The method according to claim 21, which is a batch method.

34. The method according to claim 21, which method is continuous.

* * * * *